United States Patent [19]

Tarnopolsky

[11] Patent Number: 5,139,680
[45] Date of Patent: Aug. 18, 1992

[54] METHOD FOR CONTINUOUS MULTICOMPONENT SEPARATION USING ANISOTROPIC SEPARATION BED

[75] Inventor: Yuri Tarnopolsky, 84 Pettaquamscutt Lk Rd., Narragansett, R.I. 02874

[73] Assignee: Yuri Tarnopolsky, Narragansett, R.I.

[21] Appl. No.: 713,382

[22] Filed: Jun. 5, 1991

[51] Int. Cl.$^5$ .............................................. B01D 15/08
[52] U.S. Cl. .............................. 210/656; 210/198.2; 210/767; 210/807; 55/386
[58] Field of Search ............... 210/198.2, 656, 644, 210/650, 767, 807, 263, 290, 321.72, 321.75, 420, 422, 492, 346; 55/386

[56] References Cited

U.S. PATENT DOCUMENTS

| | | | |
|---|---|---|---|
| 3,266,629 | 8/1966 | Megibow | 210/346 |
| 3,503,712 | 3/1970 | Sussman | 210/198.2 |
| 3,796,657 | 3/1974 | Pretorius et al. | 55/386 |
| 3,856,681 | 12/1974 | Huber | 210/198.2 |
| 4,176,069 | 11/1979 | Metz et al. | 210/321.75 |
| 5,015,388 | 5/1991 | Pusineri et al. | 210/492 |
| 5,032,247 | 7/1991 | Tarnopolsky | 204/299 R |

OTHER PUBLICATIONS

W. G. Sisson et al., Application of Continuous Annular Chromatography to Size-Exclusion Separations, Preparative Chromatography, 1989, vol. 1(2) pp. 139-162.
K. Hashimoto et al, Continuous Separation of Bio-Components by Rotating Annular Chromatography, Preparative Chromatography, 1989, vol. 1(2), pp. 163-177.
E. J. Tuthill, A New Concept for the Continuous Chromatographic Separation of Chemical Species, Journal of Chromatographic Science, vol. 8, 1970 pp. 285-287.

Primary Examiner—Robert A. Dawson
Assistant Examiner—Sun Uk Kim

[57] ABSTRACT

Continuous multicomponent separation is conducted in a two-dimensional anisotropic separation bed which has different separating properties in at least two directions, Y and X. The carrier fluid flows repeatedly and alternately in directions Y and X through the bed. The mixture is introduced into the flow in the vicinity of one of the corners. The components are collected through multiple outlets. An example of anisotropic bed is alternating layers of dense chromatographic packing with high separating ability and loose packing with low separating ability. Another example of anisotropic bed is tightly packed aligned fibrillar sorbent. Due to anisotropic properties of the bed, the components move along diverging resulting trajectories.

8 Claims, 8 Drawing Sheets

Dense layer
Loose layer

METHOD FOR CONTINUOUS MULTICOMPONENT SEPARATION USING ANISOTROPIC SEPARATION BED

FIELD OF INVENTION

The present invention relates to separation of mixtures of chemical compounds into components. More particularly, the present invention relates to continuous multicomponent separation of said mixtures.

DESCRIPTION OF PRIOR ART

A wide variety of modern methods of separation are currently used in research and development. Among them, gas and liquid chromatography, electrophoresis, membrane technology, ultrafiltration, liquid extraction, etc., are well known and their general description can be found in monographs, textbooks, and reviews.

For comparing the present invention with the prior art, it is essential to draw distinction between the following methods of separation:
1. Batch methods.
2. Continuous methods:
   (a) limited to separating not more than two components,
   (b) applicable for two and more components.

While the general trend of chemical industry, as well as research, is toward continuous uninterruptible production, most of the separation methods are periodical by their nature.

In a periodical, in other words, batch separation process, a certain amount of mixture is introduced into separation device prior to separation. The next amount of the mixture can be loaded only after the previous one has been processed. Most of the known methods separate components in time, i.e., the components could be collected at the same point of the separating device at consecutive segments of time.

Thus, in column chromatography, a sample is introduced at one end of a chromatographic column, a flow of a carrier fluid transports the components through a chromatographic bed, and the separated components are collected at the other end of the column in a time sequence.

If the mixture consists of only two components or two fractions of interest, some modification of the above methods can usually make the separation continuous. In such cases, two components are simultaneously collected at two different points of a linear separation device.

Simulated moving bed chromatography is an example of such continuous separation of a mixture into extract and raffinate. This method represents a case of a method which is continuous but not multicomponent.

There are very few known methods of continuous multicomponent separation. Among them, free flow electrophoresis and rotating annular chromatography are now gaining popularity. Both can perform the function of multicomponent separation.

The present invention is related to the group of separation methods which is represented by free flow electrophoresis and rotating annular chromatography. Although they are based on different principles, both are multicomponent and both use a carrier fluid to transport the components. Chromatographic separation, as well as some techniques of electrophoresis, are performed in a separation bed.

No close prior art has been found for this invention. However, since this invention and the above mentioned multicomponent continuous methods perform the same function and have common features, it is useful to examine free flow continuous electrophoresis and rotating annular chromatography in order to highlight the novelty of the approach which is taken in this invention.

All known methods of continuous multicomponent separation are two-dimensional in the sense that the process of separation displays in two geometrical dimensions, while the third dimension of the device is not relevant to the principle of the method.

In free flow continuous electrophoresis, a mixture is introduced, at a certain point, into a flow of a liquid, usually, a solution of salts in water. The components are carried with the flow toward the other end of the device. They separate under the influence of a transversal electrical field. The components move along diverging trajectories and they are collected with an array of multiple outlets.

The use of electrical current in this method narrows the field of its application to water solutions and other electrically conductive liquids, increases the consumption of energy, and rises safety requirements.

In continuous annular chromatography, which is also called rotating continuous chromatography, the mixture is introduced into a rotating annular chromatographic bed through an inlet which is fixed outside the edge of the rotating bed. The points of collection of the components are also fixed outside the other edge of the bed. Therefore, all inlets and outlets of the device are sliding along the circular edges of the annular bed. The movement of the bed creates a circular displacement of the entire bed which is transversal to the flow of the fluid in the bed.

For a detailed description of continuous annular chromatography, see W. G. Sisson, et al, Preparative Chromatography, 1(2), 139-162 (1989), and K. Hashimoto, ibid., 1(2), 163-177.

A significant disadvantage of continuous annular chromatography is its technical complexity related to the necessity of the mechanical rotation of the chromatographic bed, as well as the need to seal the stationary inlets and outlets during their relative movement with respect to the bed.

However, there is a more fundamental limitation of continuous annular chromatography. In order to be separated, the components are supposed to come out of the bed during not more than one full turn. The impurities which move much slower than the target components can make more than one full turn around the axis of the bed so that they may contaminate the purified components.

OBJECTS AND ADVANTAGES

The purpose of this invention is to achieve continuous multicomponent separation of mixtures of chemical compounds which is free of the limitations of the cited methods.

Some of the advantages of the present invention are:
(a) it is free of the necessity to employ either absolute or relative mechanical movement of the bed in respect to any part of the separation device;
(b) the inlets and outlets are fixed in respect to the separation bed;
(c) it performs separation in non-conductive as well as in conductive media;

(d) it is applicable to a wide range of mobilities of components of the mixture;

(e) it can be used not only with liquid but also with gas and supercritical fluid as carrier.

DEFINITION OF TERMS

By the term "chromatographic packing" is meant any material which is used in various techniques of chromatography as stationary phase, including particulate or fibrillar sorbent, as well as sorbent in the form of rigid, flexible, or soft porous sheet, film, paper, plate, block, etc.

By the term "two-dimensional bed" is meant the bed in which the process of separation displays in two geometrical dimensions, and the third dimension is not relevant to the principle of the separation.

By the term "anisotropic bed" is meant the two-dimensional bed which has different structure in at least two different directions, thereby providing different separating properties in said directions.

By the term "multicomponent separation" is meant simultaneous separation of more than two components.

By the term "fluid" is meant liquid, supercritical liquid, vapor, and gas.

SUMMARY OF THE INVENTION

The objective of this invention is to conduct continuous multicomponent separation without the use of any physical field such as electrical, gravitational, magnetic, or any other, as well as without any mechanical movement of the bed. Instead, the separation is conducted in a two-dimensional separation bed which has different structure in at least two different directions, thereby providing different separating properties in said directions. Said bed will be further referred to as anisotropic bed, and said directions will be referred to as the first and the second directions. The carrier fluid flows alternately in the first and the second directions through the anisotropic bed.

When the carrier fluid flows through the anisotropic bed, the bed shows different separating properties, depending on the direction of the flow.

The carrier fluid flows stepwise in the first direction, then in the second direction, then the flow continuously alternates between both directions. The mixture is introduced into the flow in the vicinity of one of the corner which is formed by the inlet edges of the bed.

Since, according to the present invention, the separating properties are different in two directions, the ratio of the displacements of a certain component in two directions is different for different components. Therefore, the components move along diverging resulting trajectories and can be collected simultaneously and continuously at different exit points.

BRIEF DESCRIPTION OF THE DRAWINGS

FIGS. 3, A and B, is a cross-section view of a stratified anisotropic bed, according to this invention.

DETAILED DESCRIPTION OF THE INVENTION

The principle of this invention would be better illustrated if compared with regular thin layer chromatography, which is normally performed on a two-dimensional isotropic bed.

Figure 1:
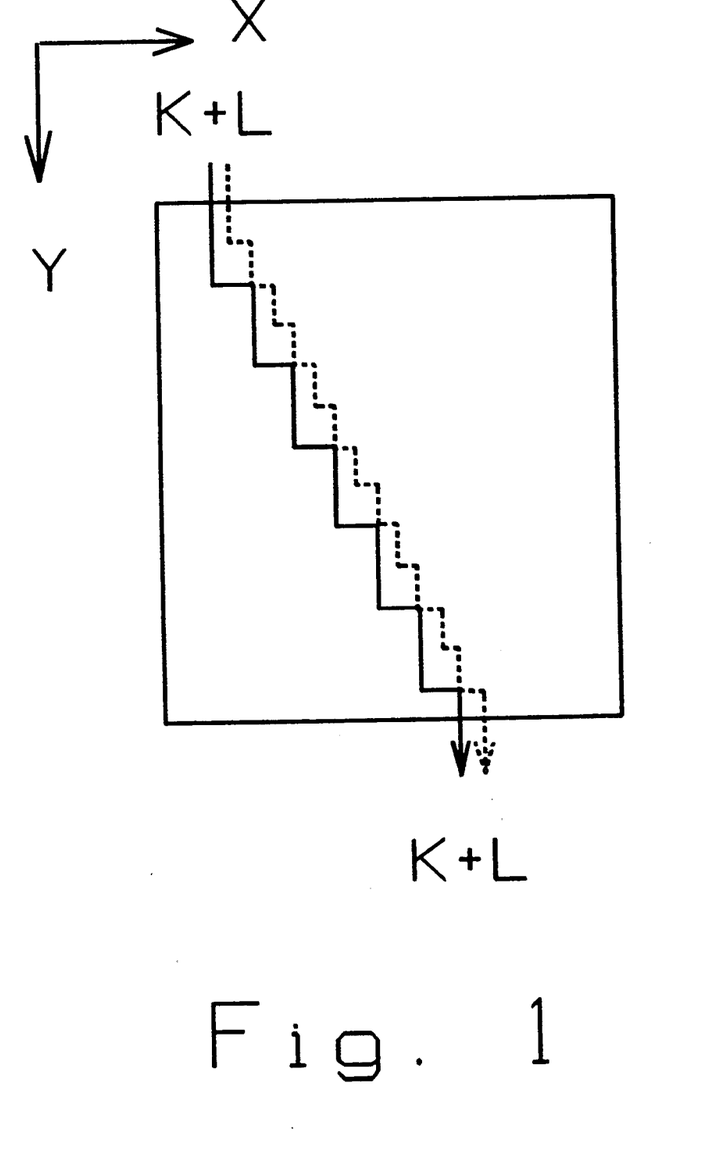
FIG. 1 illustrates separation of two components on an isotropic two-dimensional bed.

In FIG. 1, the mixture of components K and L is introduced into the same area on a rectangular isotropic chromatographic plate. The planar flow of the carrier fluid alternates between directions Y and X.

In FIG. 1 the points of introduction of each component and the pathways of the components are shown slightly displaced, for the purpose of better illustration.

The retention of a given component by the bed depends on the properties of the component, the bed, and the carrier. Therefore, the ratio of the displacements of two components in each direction is the same. For the purpose of illustration, it is taken 2:1 for K and L, respectively. In other words, component L is retained by the bed twice as much as component K.

It is obvious, that for any isotropic bed it is impossible to separate the components in a continuous way by alternating the direction of the carrier fluid.

FIG. 1 is not related to the present invention. It is used to explain the principle of this invention in a comparative fashion.

Figure 2:
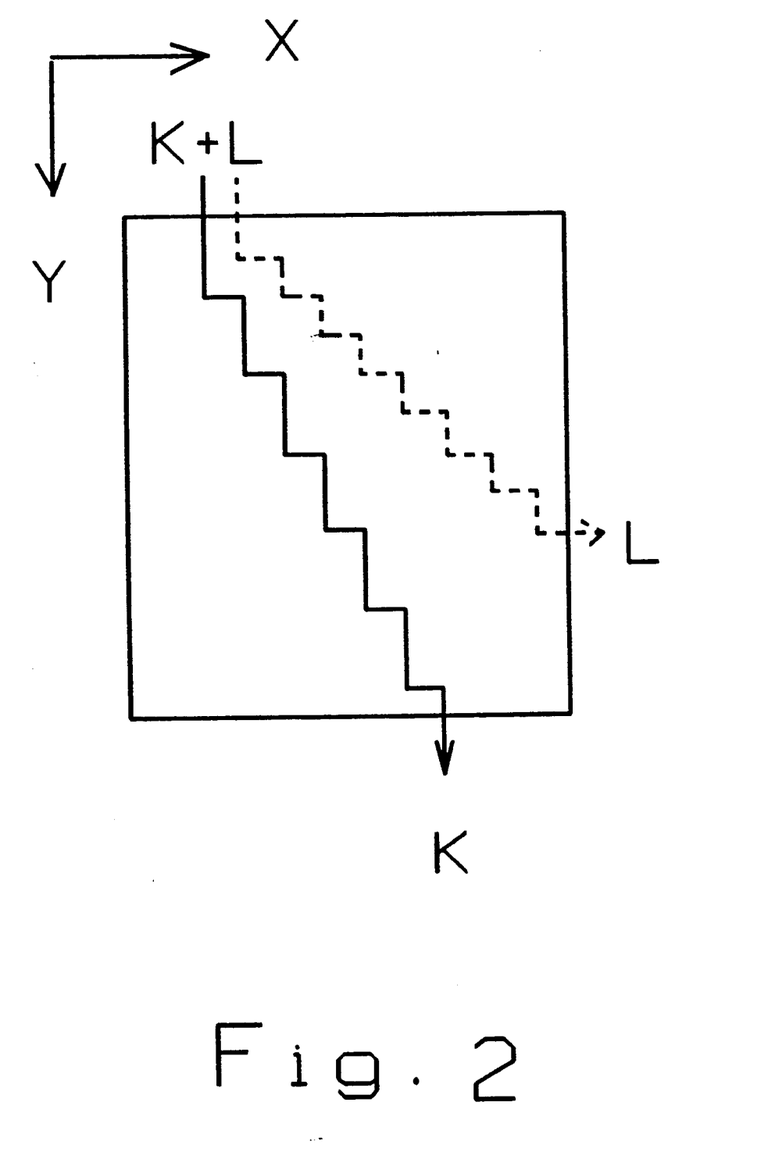
FIG. 2 illustrates separation of two components on an anisotropic two-dimensional bed, according to this invention.

In FIG. 2, components K and L are introduced into an anisotropic bed, which is comprised by this invention. The carrier fluid alternates between two directions, Y and X, as in the previous case. The ratio of displacements of two components in direction Y is shown 2:1 for K and L, respectively. In direction X, this ratio is shown 1:1, for the purpose of illustrating different separating properties in both direction. The components, therefore, move along diverging trajectories and can be collected separately.

It is obvious, that the anisotropy of separating properties is a necessary condition for the components to be separated in a sequence of alternating movements of the carrier fluid through a two-dimensional bed.

This invention comprises an anisotropic bed, which can be designed in a number of ways. Here, two preferred embodiments of the anisotropic bed will be described.

Figure 3:
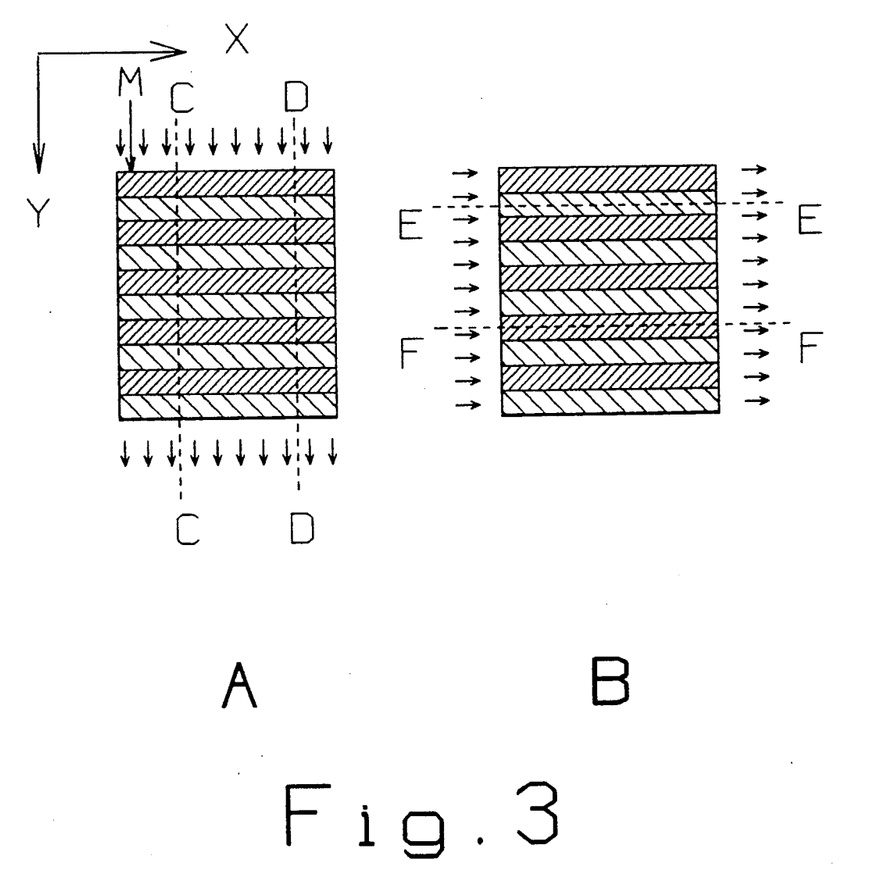

FIG. 3, A and B, show an anisotropic bed which consists of alternating dense and loose layers of packing. This anisotropic bed will be further referred to as the stratified bed. The dense layers are hatched denser than the loose ones. First and second directions of the flow are shown by arrows Y and X, respectively. Arrow M indicates the point of introduction of the mixture. FIG. 3A relates to the flow of the fluid carrier in the first direction (Y). FIG. 3B relates to the flow of the fluid carrier in the second direction (X).

The dense layer is filled with chromatographic packing. Many regular chromatographic packings show high resistance to the flow and high selectivity to components. The chromatographic packing for the dense layers of this invention can be particulate, as well as in the form of solid porous blocks, plates, sheets, films, paper, membranes, etc. A number of non-particulate chromatographic packings and membranes, such as particles of sorbent embedded into a porous sheet, which can be used in this invention, have been developed in recent years.

The loose layer is filled with a packing which shows low resistance to the flow and low or none selectivity. The examples of the packing for the loose layer are: glass beads, sand, glass wool, glass frit, synthetic wool and felt, plastic mesh, plastic spacer mesh which is normally used in membrane technology and cross-flow filtration, porous ceramic plates, porous metal, etc.

Ideally, the loose packing is not supposed to have chromatographic selectivity, and, in general, should be non-adsorbing toward the components of the mixture. However, for the realization of this invention, it does not need to be ideal in this aspect.

When a fluid flows in direction Y, which is first direction, the bed shows different chromatographic properties than when the fluid flows in direction X, which is second direction.

The difference is that the flow in the first direction (Y) is uniform because the bed shows equal resistance to the flow and equal separating properties along any line which is parallel to the flow. Thus, the separating properties of the bed are the same along the line CC, as well as along the line DD, see FIG. 3A.

When the carrier fluid flows in the second direction (X), different parts of the flow pass through layers with different separating properties. Thus, the separating properties along the line EE and along the line FF, are different, see FIG. 3B.

At the same time, dense and loose layers show different resistance to the fluid flow. The flow in the second direction (X) will not be uniform. The more different the loose and dense layers are the more flow will go through the loose layers comparing with the flow through the dense layers.

Therefore, in the first direction, the components separate when they pass through the dense layers. They are transported without significant separation when they pass through the loose layers in the same direction.

When they move in the second direction, however, they pass mostly through the loose layers, in which they are transported without significant separation.

At any given moment, the components are distributed between the dense and the loose layers. They separate, essentially, in the first direction. They are, essentially, indiscriminately transported in the second direction.

Figure 4:
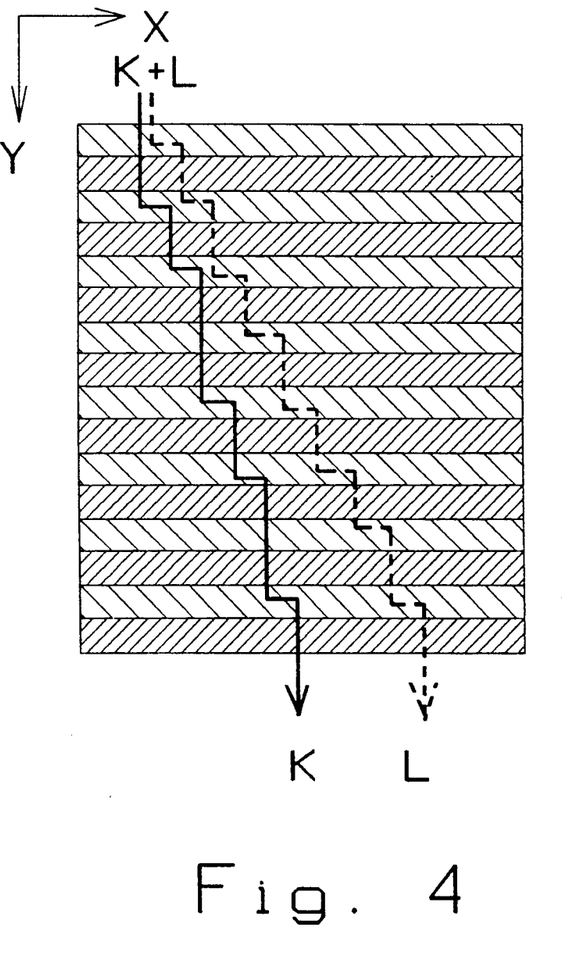
FIG. 4 schematically shows the process of separation of two components in a stratified anisotropic bed, according to this invention.

FIG. 4 shows how two components, K and L, can be separated in a stratified anisotropic bed. The segments of the pathways vary in length in the first direction (Y) because when a component is in a dense layer, it misses the displacement in the second direction (X) during the displacement of the carrier fluid in that direction.

Due to diffusion and continuous introduction, any component at a given moment is present in both loose and dense layers. However, the flow of the carrier fluid in the second direction gradually washes all the components in that direction. Since the components move in the first direction with different velocities, they are separated, as shown in FIG. 4.

To summarize, the stratified anisotropic bed works in the following way, see FIGS. 3 and 4.

Step 1

The carrier fluid flows through the bed in the first direction, which is shown by arrow Y. In this flow, a mixture is introduced at a limited area in the vicinity of the corner which is formed by the inlet edges of the bed. The area of introduction can be inside a loose layer, a dense layer, or in both at the same time.

Step 2

The carrier fluid flow changes the direction from the first one to the second one, which is shown by arrow X. The mixture may or may not be injected during this step.

Step 3

Alternate repetition of steps 1 and 2, respectively.

The components are continuously and simultaneously collected at appropriate outlets along on or both outlet edges of the bed. The injection of the mixture can be continuous, intermittent, or pulsating.

As it can be concluded from the above description, the fact that the bed has stratified structure is not a necessary condition to the principle of the invention, which comprises any anisotropic chromatographic bed.

Figure 5:
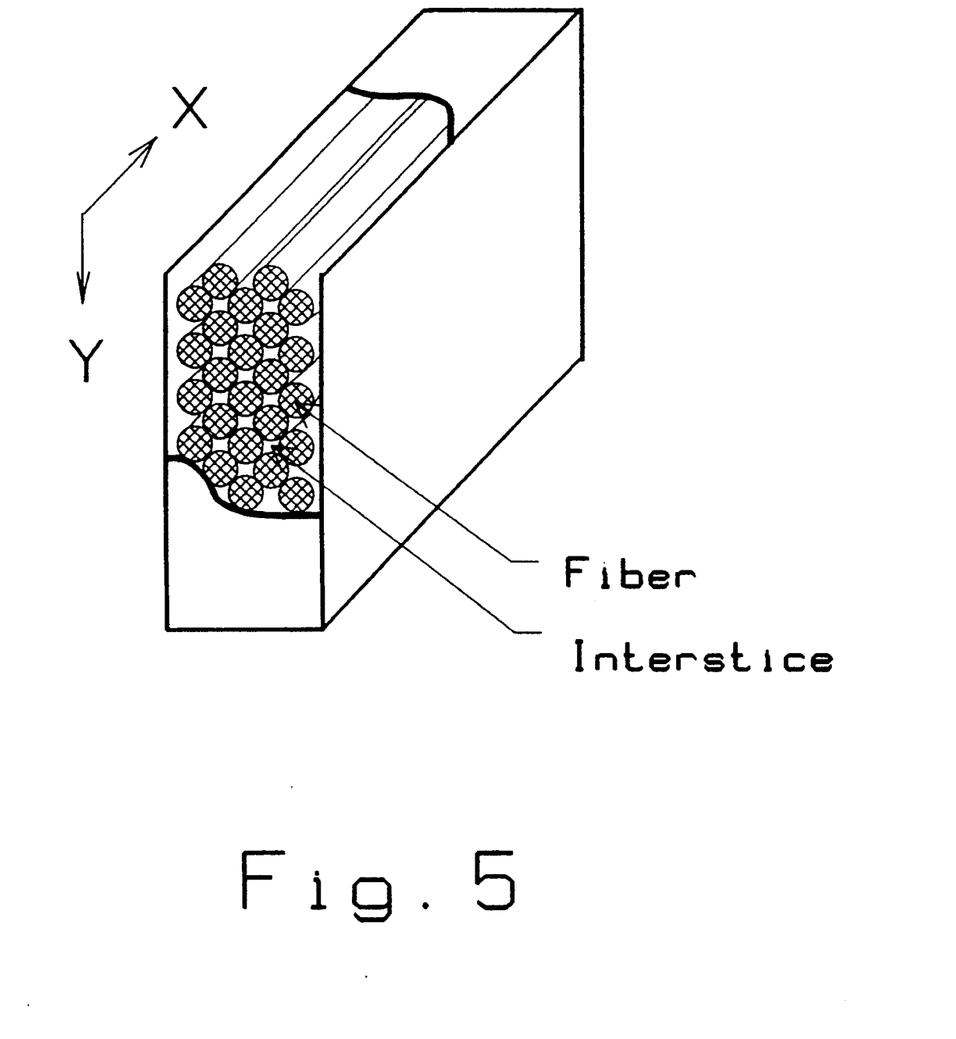
FIG. 5 is an exaggerated perspective view of a fibrillar anisotropic bed, according to this invention.

FIG. 5 shows a two-dimensional chromatographic bed which is tightly packed with aligned porous fiber made of chromatographically active material such as silica fiber, porous synthetic organic fiber, etc. This bed will be further referred to as the fibrillar bed.

The fiber is aligned in the second direction. Porous silica fiber and porous plastic fiber are examples of material for the packing.

When the carrier fluid moves in the first direction which is shown by arrow Y, it goes across the fiber, essentially, through the pores. It interacts with the bulk of the packing, and the components are separated in this direction. However, when the fluid moves in the second direction, which is shown by arrow X, the preferred pathway is through the interstices where both the resistance to the flow and the surface of interaction is minimal.

As it can be seen from the above description, the regularity of the alternation of dense and thick layers, as well as their planar shape and co-planar orientation is not a necessary condition for the invention. The requirement that the separation bed has anisotropic properties could be met in different ways.

For example, the anisotropic bed can be made of oriented elongated particles, oriented short pieces of fiber, and solid porous plate with multiple aligned channels. It can be made as a thin layer chromatography plate with aligned alternating strips of sorbent and inert porous material.

The material for the dense layers should not necessarily be a chromatographic packing. The necessary requirement is that the dense layer possesses separating abilities and is permeable to the flow.

Furthermore, the composition and the properties of both kinds of layers, independently or in combination, can vary in a given direction, so that a gradient of a certain property is formed within a bed. For example, the dense layers can be a set of filtration screens with the size of the mesh which gradually decreases in the first direction.

Any anisotropic properties, as far as separation is concerned, would do, and the above examples should not be considered as limiting the scope of the invention.

DESCRIPTION OF PREFERRED EMBODIMENTS

Figure 6:
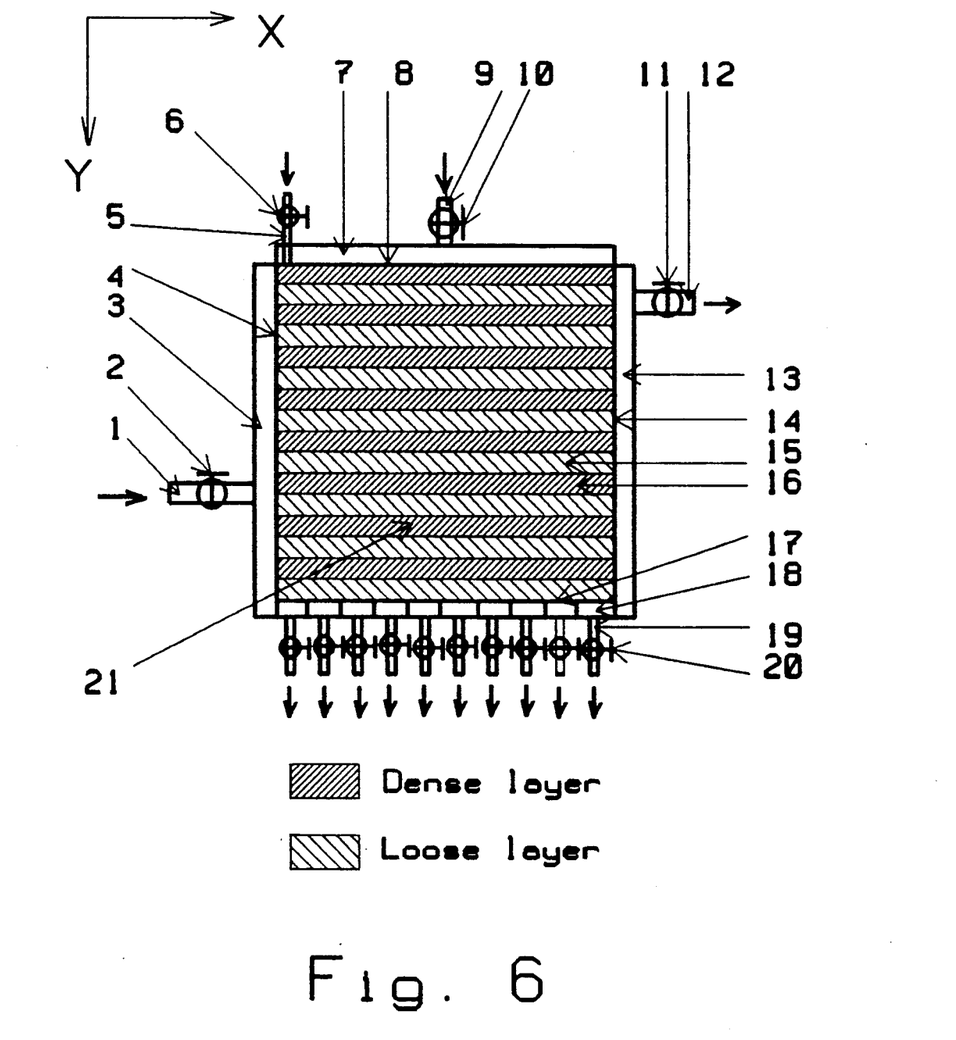
FIG. 6 is a cross-section of a preferred embodiment of an apparatus for this invention.
Figure 7:
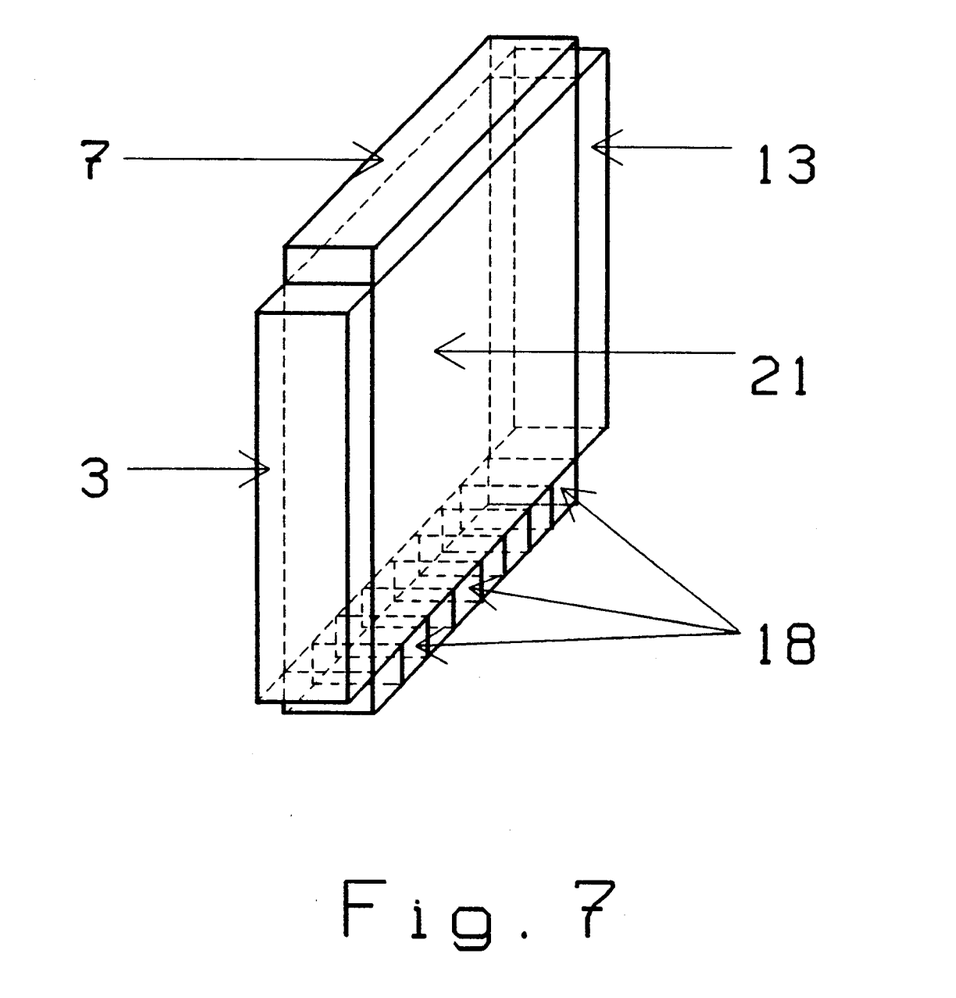
FIG. 7 is a perspective view of the chambers of a preferred embodiment of an apparatus for this invention.

A preferred embodiment of the device, according to this invention, is schematically illustrated in FIGS. 6 and 7.

FIG. 6 shows a cross-section of the device. A rectangular separating device consists of the main chamber 21 which is formed by two solid walls, the front wall and the back walls, which are not seen. Both solid walls are parallel to the plane of the drawing and perpendicular to four uniformly permeable walls, in other words, frits 4, 8, 14, and 17. Porous stainless steel, glass, ceramics, and plastics could be mentioned as examples of porous materials for the permeable walls.

The frits 4, 8, 14, and 17 separate the main chamber from feeding chambers 3 and 7, as well as from collecting chamber 13 and a plurality of identical collecting chambers 18. Each of said chambers 18 has inlets 1 and 9, correspondingly, and outlets 12 and 19, correspondingly. The inlets and outlets have valves 2, 10, 11, and 20, correspondingly. Inlet 5, with valve 6, goes directly inside the separation chamber.

The mutual arrangement of chambers 3, 7, 13, 18, and 21 is shown separately in FIG. 7.

In FIG. 6, arrows Y and X show first and second direction, correspondingly.

Main chamber 21 encloses a stratified anisotropic bed, as described above. In FIG. 6, the loose layers 15 and dense layers 16 layers are hatched differently, with the notation of the hatch given at the bottom of FIG. 6.

Any anisotropic bed could be used with this device.

The separating device works through the following sequence of steps.

Before the start, all chambers of the device are filled with a fluid which serves as a carrier. In gas chromatography it is the carrier gas, in supercritical fluid chromatography it is the supercritical fluid, in liquid chromatography it is the solvent.

STEP 1

Valve 10 and valves 20 are open. Valve 2 and valve 11 are closed. The carrier fluid is injected through inlet 9. The fluid enters main chamber 21 through frit 8, moves in the direction of arrow Y inside main chamber 21, leaves main chamber 21 through frit 17, and comes out through multiple outlets 19.

Simultaneously, a mixture to be separated is injected into main chamber 21 through inlet 5 and valve 6. The mixture itself could be gas, vapor, liquid, or supercritical fluid, depending on the application of the invention.

The injection of the mixture could take less time than the injection of the fluid. This step is equivalent to mixture injection in batch chromatography.

STEP 2

After certain amounts of the carrier fluid and the mixture have been injected, valves 5, 10 and multiple valves 20 are closed. Valves 2 and 11 are open. The fluid is injected through valve 2. It enters chamber 21 through frit 4, moves in the direction of arrow X, and leaves it through frit 14, chamber 13, and outlet 12.

STEP 3

Steps 1 and 2 are continuously repeated.

The amount of the carrier fluid which is introduced at one step should be essentially less than the void volume of the main chamber.

When components reach frit 17, they are separated in space and are continuously collected through outlets 20.

In another preferred embodiment, chamber 13 is separated into compartments and has a multitude of outlets with valves, similar to chamber 18, outlets 19, and valves 20. Therefore, the components could be collected along both outlet edges of the bed, as shown in FIG. 5.

The number of multiple outlets and the number of dense and loose layers of the bed depends on the desired degree of resolution.

Computer simulation of the separation process, according to this invention, shows that in order to achieve separation, the linear displacement of the carrier fluid during step 1, i.e., in direction Y in FIG. 6, should be more than over one pair of loose and dense layers. The value of this displacement at a given bed, as well as the number of layers, are important parameters for separation. For a better separation, a large number of layers per unit of dimension is preferred.

Figure 8:
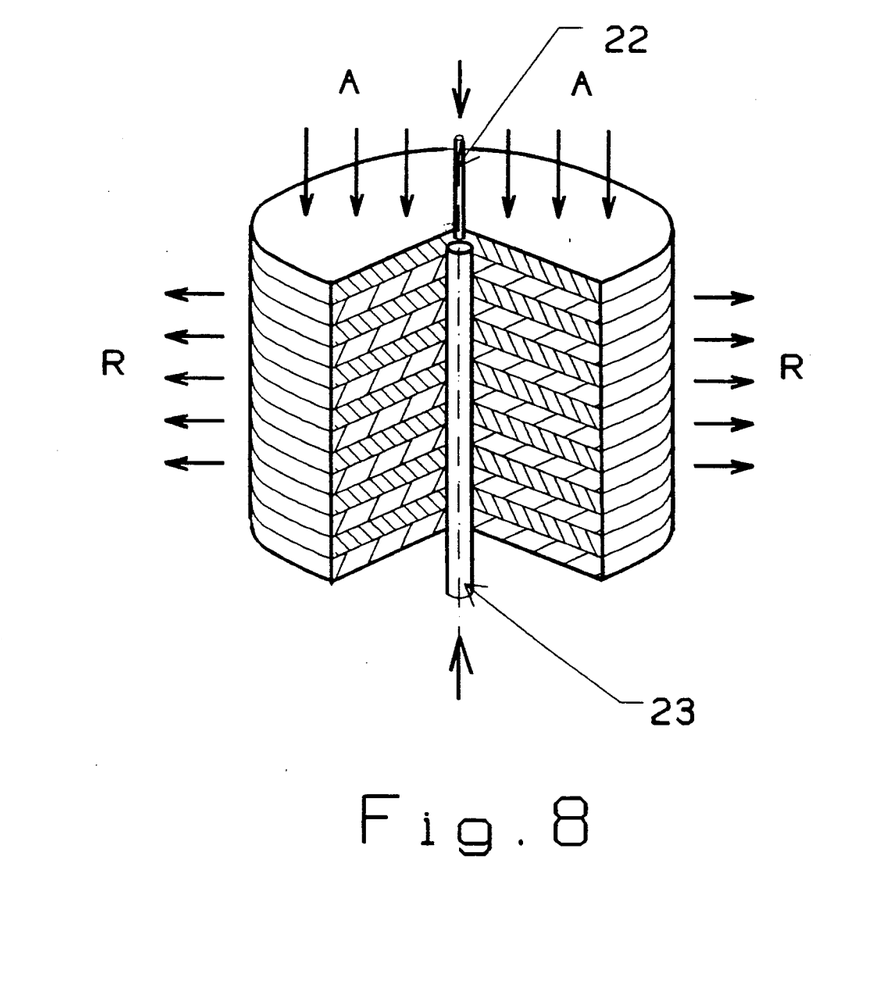
FIG. 8 is a perspective view and sectoral cross-section of the anisotropic bed in another preferred embodiment of this invention.

In yet another preferred embodiment, dense and loose layers are made in the form of alternating co-planar discs so that they form a cylinder, as it is shown in FIG. 8. The mixture is injected through tube 22. In this embodiment, the fluid alternatively takes part in radial flow toward the external wall, arrows R, and in axial flow, arrows A. Pipe 23 is closed at the upper end. It serves as the inlet for the radial flow. The part of tube 23 which is inside the bed is porous in order to distribute the flow evenly along the axis of the device. The carrier fluid and components could be collected through circular compartments of the annular collecting chamber, which are not shown.

In yet another preferred embodiment, the two-dimensional anisotropic bed is coiled around the axis which is either perpendicular or parallel to the layers, so that it can take less space at the same separating area. The feeding and collecting chambers for one of the directions can be made in the form of disks which cover the butt-ends of the roll.

The description above should not be regarded as limiting the scope of the invention which should be determined solely by the appended claims.

I claim:

1. A method of continuous separation of a mixture of chemical compounds in a carrier fluid flowing through a two-dimensional separation bed, said mixture being continuously or intermittently introduced into said bed, and separated components being continuously collected at multiple outlets, wherein said bed comprises a packing having different structure in at least two different directions, thereby providing different separating properties in said directions, and said carrier fluid flows alternately and repeatedly in both said directions.

2. The method of claim 1 wherein said packing having different structure in at least two different directions comprises a plurality of alternating layers of at least two kinds, one of said kinds having higher resistance to fluid flow and higher ability to separate components of the mixture than the other one, thereby providing different separating properties in the directions which are, essentially, perpendicular and parallel to said layers.

3. The method of claim 2 wherein said layers of the kind which has higher resistance to the fluid flow and higher ability to separate components of mixture than the other one are selected from the group consisting of particulate chromatographic packing, permeable membranes, solid porous plates of sorbent material, particulate sorbent material embedded into porous sheets, permeable film, paper, and their combinations.

4. The method of claim 2 wherein said layers of the kind which has lower resistance to the fluid flow and lower ability to separate components of mixture than the other one are selected from the group consisting of glass beads, sand, glass wool, synthetic fiber felt, glass frit, plastic mesh, and their combinations.

5. The method of claim 2 wherein said alternating layers of at least two kinds have a shape of stacked disks, thereby providing different separating properties in radial and axial directions.

6. The method of claim 1 wherein said packing having different structure in at least two different directions comprises aligned porous fiber, thereby providing different separating properties in directions perpendicular and parallel to the fiber.

7. The method of claim 6 wherein said aligned porous fiber is selected from the group consisting of porous silica fiber and porous synthetic organic fiber.

8. The method of claim 1 wherein said packing having different structure in at least two different directions comprises solid porous material having the property of chromatographic separation of mixtures and a plurality of aligned channels going through said material in, essentially, one direction, thereby providing different separating properties in directions perpendicular and parallel to said channels.

* * * * *